(12) United States Patent
Wang

(10) Patent No.: US 12,299,434 B2
(45) Date of Patent: May 13, 2025

(54) SOFTWARE UPGRADING METHODS AND SYSTEMS FOR MEDICAL DEVICES

(71) Applicant: SHANGHAI UNITED IMAGING HEALTHCARE CO., LTD., Shanghai (CN)

(72) Inventor: Tian Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 110 days.

(21) Appl. No.: 18/067,013

(22) Filed: Dec. 15, 2022

(65) Prior Publication Data

US 2023/0195446 A1      Jun. 22, 2023

(30) Foreign Application Priority Data

Dec. 16, 2021   (CN) .......................... 202111541746.X

(51) Int. Cl.
| | | |
|---|---|---|
| G06F 9/445 | (2018.01) | |
| G06F 8/65 | (2018.01) | |
| G06F 9/455 | (2018.01) | |
| G06F 11/00 | (2006.01) | |
| G06K 7/14 | (2006.01) | |
| G16H 40/40 | (2018.01) | |

(52) U.S. Cl.
CPC .............. *G06F 8/65* (2013.01); *G16H 40/40* (2018.01)

(58) Field of Classification Search
CPC ..... G06F 8/65; G06F 8/60; G06F 8/63; G06F 9/4401; G06F 8/71; G06F 8/68; G06F 11/1417; G06F 9/4408; G06F 8/61; G06F 11/1433; G16H 40/40; G16H 40/67; A61N 1/3993; A61N 1/3968; A61N 1/0484; A61B 5/332; H04L 67/34; G01N 33/48792
See application file for complete search history.

(56) References Cited

U.S. PATENT DOCUMENTS

| | | |
|---|---|---|
| 6,363,282 B1 | 3/2002 | Nichols et al. |
| 7,770,164 B2 | 8/2010 | Schuelein et al. |
| 8,051,414 B2 * | 11/2011 | Stender ................... G16H 40/40 |
| | | 717/168 |
| 8,190,445 B2 | 5/2012 | Kuth et al. |
| 8,392,902 B2 | 3/2013 | Reinz |
| 8,770,482 B2 * | 7/2014 | Ackermann ..... G01N 33/48792 |
| | | 235/449 |
| 8,893,109 B2 | 11/2014 | Birtwhistle et al. |
| 8,977,016 B2 | 3/2015 | Jones et al. |
| 9,747,653 B2 | 8/2017 | Haider et al. |

(Continued)

FOREIGN PATENT DOCUMENTS

| | | |
|---|---|---|
| CN | 105988812 A | 10/2016 |
| CN | 108268270 B | 7/2021 |
| EP | 2740061 B1 | 3/2018 |

*Primary Examiner* — Thuy Dao
(74) *Attorney, Agent, or Firm* — METIS IP LLC

(57) ABSTRACT

The embodiments of the present disclosure provide a method for device software component. The method may include receiving, from an operating terminal of a target device, a target request with respect to a target software component; determining a target file of the target software component based on the target request; and transmitting the target file to the operating terminal of the target device to cause the operating terminal to perform a software processing operation on the target device based on the target file.

16 Claims, 12 Drawing Sheets

500

- 510: Receiving, from an operating terminal of a target device, a target request with respect to a target software component
- 520: Determining a target file of the target software component based on the target request
- 530: Transmitting the target file to the operating terminal of the target device to cause the operating terminal to perform a software processing operation on the target device based on the target file

(56) References Cited

U.S. PATENT DOCUMENTS

| | | |
|---|---|---|
| 10,861,597 B2 | 12/2020 | Norris et al. |
| 10,861,600 B2 | 12/2020 | Warner et al. |
| 11,081,232 B2 | 8/2021 | Aysin et al. |
| 11,169,794 B2 | 11/2021 | Kiaie et al. |
| 12,002,576 B2 * | 6/2024 | Hulan .................... G16H 40/40 |
| 2007/0021977 A1 | 1/2007 | Elsholz |
| 2008/0046378 A1 | 2/2008 | Harrison et al. |
| 2008/0184219 A1 | 7/2008 | Matsumoto |
| 2010/0280847 A1 | 11/2010 | Schaffer |
| 2011/0209139 A1 | 8/2011 | Dominick et al. |
| 2011/0307274 A1 | 12/2011 | Thompson et al. |
| 2011/0320595 A1 | 12/2011 | Konishi et al. |
| 2013/0036415 A1 | 2/2013 | Birtwhistle |
| 2013/0253600 A1 | 9/2013 | Drew et al. |
| 2014/0229221 A1 * | 8/2014 | Shih ................ G06Q 10/06312 705/7.23 |
| 2014/0280462 A1 | 9/2014 | Gharabally et al. |
| 2015/0019257 A1 | 1/2015 | Doyle et al. |
| 2016/0155167 A1 | 6/2016 | Kim et al. |
| 2016/0294951 A1 | 10/2016 | Durrant et al. |
| 2017/0017479 A1 | 1/2017 | Hedmann et al. |
| 2018/0032675 A1 | 2/2018 | Dominick et al. |
| 2021/0125713 A1 * | 4/2021 | Audrain ................ A61M 5/172 |
| 2021/0158962 A1 | 5/2021 | Allassonniere et al. |
| 2021/0335479 A1 | 10/2021 | Liang et al. |
| 2021/0373871 A1 | 12/2021 | Manuel |

* cited by examiner

500

```
┌─────────────────────────────────────────────────┐
│ Receiving, from an operating terminal of a target│ 510
│ device, a target request with respect to a target│
│           software component                     │
└─────────────────────────────────────────────────┘
                        │
                        ▼
┌─────────────────────────────────────────────────┐ 520
│ Determining a target file of the target software │
│       component based on the target request      │
└─────────────────────────────────────────────────┘
                        │
                        ▼
┌─────────────────────────────────────────────────┐ 530
│ Transmitting the target file to the operating terminal│
│ of the target device to cause the operating terminal │
│ to perform a software processing operation on the   │
│         target device based on the target file      │
└─────────────────────────────────────────────────┘
```

610 Obtaining account information of an account logged in through a user terminal, the account being bound with the target device

620 Determining at least one medical device bound with the account, the at least one medical device including the target device

630 For one or more of the at least one medical device, determining at least one available software component

640 Receiving a candidate request with respect to the at least one available software component from the user terminal

650 Determining a candidate software component based on the candidate request

┌─────────────────────────────────────────────────┐
│ Obtaining predictive usage information of the target │ 1110
│ device within a target time period              │
└─────────────────────────────────────────────────┘
                        ↓
┌─────────────────────────────────────────────────┐
│ Determining a processing duration of the target │ 1120
│ software component based on the target file     │
└─────────────────────────────────────────────────┘
                        ↓
┌─────────────────────────────────────────────────┐
│ Determining a processing time schedule based on │ 1130
│ the predictive usage information and the processing │
│ duration                                        │
└─────────────────────────────────────────────────┘

FIG. 11

SOFTWARE UPGRADING METHODS AND SYSTEMS FOR MEDICAL DEVICES

CROSS-REFERENCE TO RELATED APPLICATIONS

This application claims priority to Chinese Patent Application No. 202111541746.X, filed on Dec. 16, 2021, the contents of which are incorporated herein by reference.

TECHNICAL FIELD

The present disclosure relates to software technology field, and in particular, to software upgrading systems and methods for medical devices.

BACKGROUND

With the development of medical devices, the use environment becomes more and more complex and operating software components installed on the medical devices are increasing more. Therefore, the operating software components need to be processed regularly to adapt to various medical requirements. Generally, due to the differences among various medical devices, it is necessary to process the software components manually on-site or remotely controlling the operating terminal by a device manufacturer, which not only wastes time and energy but also results in that users have poor autonomy and selectivity for the software components, resulting in low processing efficiency. Therefore, it is desirable to provide software upgrading systems and methods for medical devices, thereby improving the autonomy and selectivity of the users and the software processing efficiency.

SUMMARY

One aspect of the present disclosure may provide a software upgrading method for a medical device. The method may include: receiving, from an operating terminal of a target device, a target request with respect to a target software component; determining a target file of the target software component based on the target request; and transmitting the target file to the operating terminal of the target device to cause the operating terminal to perform a software processing operation on the target device based on the target file.

Another aspect of the present disclosure may provide a software upgrading system for a medical device. The system may include: at least one storage device including a set of instructions; and at least one processor configured to communicate with the at least one storage device, wherein when executing the set of instructions, the at least one processor is configured to direct the system to perform operations including receiving, from an operating terminal of a target device, a target request with respect to a target software component; determining a target file of the target software component based on the target request; and transmitting the target file to the operating terminal of the target device to cause the operating terminal to perform a software processing operation on the target device based on the target file.

Another aspect of the present disclosure may provide a non-transitory computer readable medium. The non-transitory computer readable medium may comprise executable instructions that, when executed by at least one processor, direct the at least one processor to perform a method, the method may comprise: receiving, from an operating terminal of a target device, a target request with respect to a target software component; determining a target file of the target software component based on the target request; and transmitting the target file to the operating terminal of the target device to cause the operating terminal to perform a software processing operation on the target device based on the target file.

BRIEF DESCRIPTION OF THE DRAWINGS

The present disclosure is further illustrated in terms of exemplary embodiments, and these exemplary embodiments are described in detail with reference to the drawings. These embodiments are not restrictive. In these embodiments, the same number indicates the same structure, wherein:

FIG. 5 is a flowchart illustrating an exemplary process for device software processing according to some embodiments of the present disclosure;

FIG. 6 is a flowchart illustrating an exemplary process for determining a candidate software component according to some embodiments of the present disclosure;

FIG. 11 is a flowchart illustrating an exemplary process for determining a processing time schedule of a target software component according to some embodiments of the present disclosure.

DETAILED DESCRIPTION

Figure 1:
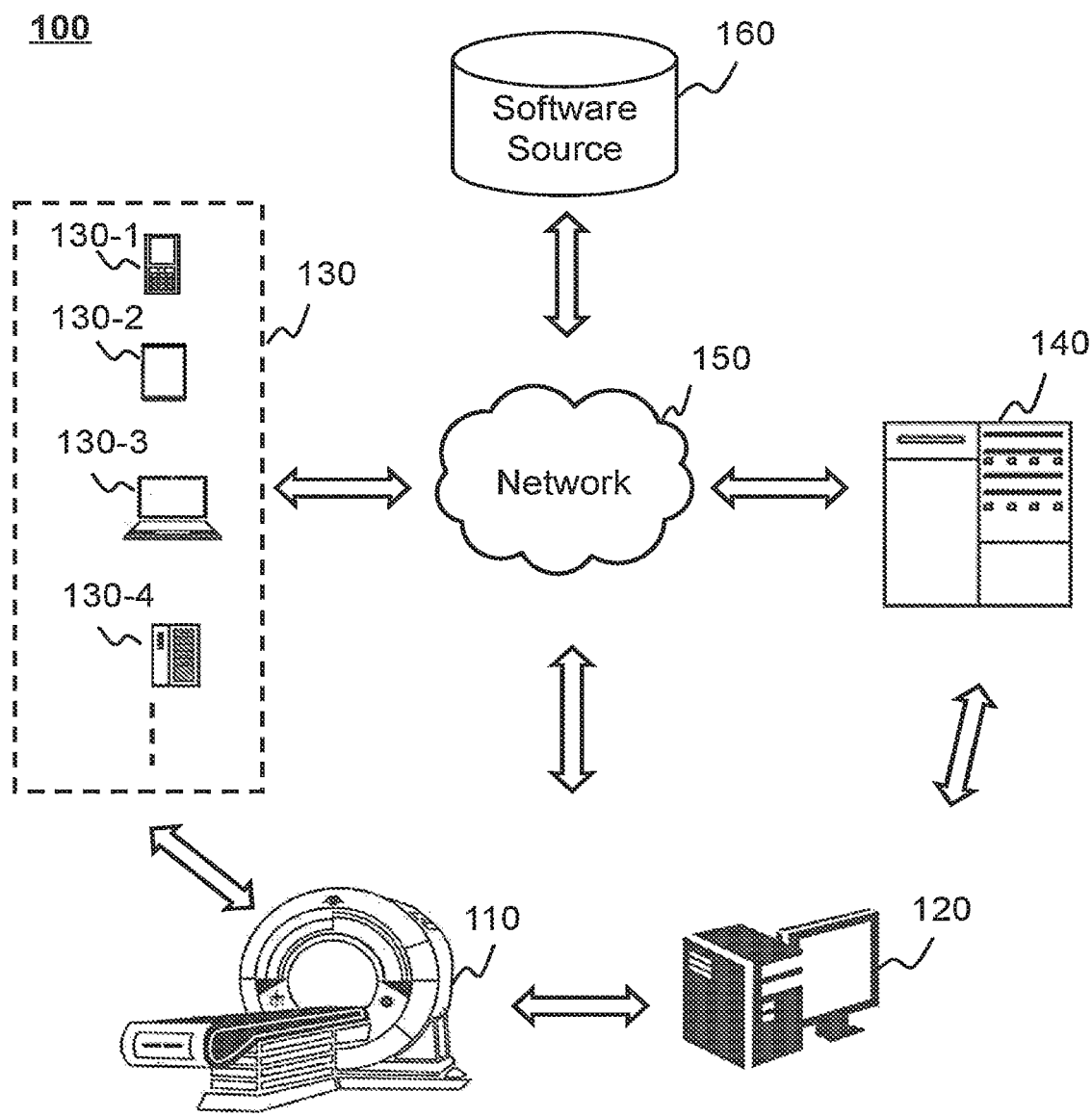
FIG. 1 is a schematic diagram illustrating an exemplary device software processing system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

Spatial and functional relationships between elements (e.g., between layers) are described using various terms, including "connected," "engaged," "interfaced," and "coupled." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

In the present disclosure, "performing a software processing operation" and "processing a software component" can be used interchangeably.

An aspect of the present disclosure relates to systems and methods for device software processing. The system may receive, from an operating terminal of a target device, a target request with respect to a target software component; determine a target file of the target software component based on the target request; and transmit the target file to the operating terminal of the target device to cause the operating terminal to perform a software processing operation on the target device based on the target file. In some embodiments, the target software component may be among at least one candidate software component. In some embodiments, the system may also determine a candidate software component from at least one available software component based on a candidate request ((also referred to as a "candidate adding instruction")) from a user terminal. According to the systems and methods of the present disclosure, the software processing (e.g., installation, update, uninstallation) can be realized independently through the operating terminal of the medical device without transferring required files through a storage device. Further, a user can view and browse updating conditions of software components that match the medical device anytime and anywhere and make independent choices through a user terminal, which can improve the efficiency and flexibility of the medical device software processing.

FIG. 1 is a schematic diagram illustrating an exemplary device software processing system according to some embodiments of the present disclosure. As shown in FIG. 1, the device software processing system 100 may include a target device 110, an operating terminal 120, a user terminal 130, a processing device 140, a network 150, and a software source 160.

The target device 110 may refer to a device on which a software processing operation (e.g., software installation, software update, software uninstallation) needs to be performed. In some embodiments, the target device 110 may include a medical device. In some embodiments, the medical device may include a single modality imaging device and/or a multi-modality imaging device. The single modality imaging device may include an X-ray imaging device, a computed tomography (CT) device, a magnetic resonance imaging (MRI) device, a radiation therapy device, or the like, or any combination thereof. The multi-modality imaging device may include an X-ray imaging-magnetic resonance imaging (X-ray-MRI) device, a positron emission tomography-X-ray imaging (PET-X-ray) device, a single photon emission computed tomography-magnetic resonance imaging (SPECT-MRI) device, a positron emission tomography-computed tomography (PET-CT) device, etc.

The operating terminal 120 may be configured to control the target device 110. In some embodiments, the operating terminal 120 may perform or determine an operation (e.g., a target request with respect to a target software component) associated with software processing of the target device 110. In some embodiments, the operating terminal 120 may perform the software processing operation (e.g., software installation, software update, software uninstallation). In some embodiments, the operating terminal 120 may be bound with the target device 110. In some embodiments, the operating terminal 120 may be an operating console of the target device 110. For example, if the target device 110 is an MRI device, the operating terminal 120 may be an operating console corresponding to the MRI device.

The user terminal 130 may be a user terminal device associated with the target device 110. In some embodiments, a user may log in an account and browse contents associated with software components through the user terminal 130. In some embodiments, the user terminal 130 may perform or determine an operation (e.g., a candidate request with respect to an available software component) associated with software processing. In some embodiments, the user terminal 130 may include a mobile device 130-1, a tablet computer 130-2, a notebook computer 130-3, a desktop computer 130-4, other devices with input and/or output functions, or any combination thereof. In some embodiments, the user terminal 130 may be integrated into the operating terminal 120. In some embodiments, the user terminal 130 may share some functions with the operating terminal 120.

The processing device 140 may process data and/or information obtained from other components of the device software processing system 100. In some embodiments, the processing device 140 may perform exemplary methods or processes described in the present disclosure based on program instructions and/or the obtained data or information. For example, the processing device 140 may receive, from the operating terminal 120 of the target device 110, a target request with respect to a target software component. The processing device 140 may determine a target file of the target software component based on the target request. Further, the processing device 140 may transmit the target file to the operating terminal 120 to cause the operating terminal 120 to perform a software processing operation on the target device 110 based on the target file.

In some embodiments, the processing device 140 may include a central processing unit (CPU), a digital signal processor (DSP), a system on a chip (SoC), a microcontroller unit (MCU), or the like, or any combination thereof. In some embodiments, the processing device 140 may be a single server or a server group. The server group may be centralized or distributed. In some embodiments, the processing device 140 may be local or remote. For example, the processing device 140 may access information and/or data stored in the target device 110, the operating terminal 120, the user terminal 130, and/or the software source 160 via the network 150. As another example, the processing device 140 may be directly connected to the target device 110, the operating terminal 120, the user terminal 130 and/or the software source 160, to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the processing device 140 may act as a software component management platform. For example, the processing device 140 may release and/or maintain software components and relevant information and a user can view and/or browse the relevant information through the operating terminal 120 and/or the user terminal 130. Merely for example, the software component management platform may be a management platform for medical applications.

The network 150 may facilitate exchange of information and/or data. In some embodiments, one or more components of the device software processing system 100 may send information and/or data to other component(s) of the device software processing system 100 via the network 150. For example, the processing device 140 may receive a target addition instruction with respect a target software component from the operating terminal 120 of the target device 110 via the network 150 and transmit a target file of the target software component to the operating terminal 120 via the network 150. In some embodiments, the network 150 may be any type of wired or wireless network, or a combination thereof. In some embodiments, the network 150 may include cable network, fiber network, telecom network, Internet, local area network (LAN), wide area network (WAN), wireless Local area network (WLAN), metropolitan area network (MAN), public switched telephone network (PSTN), Bluetooth network, ZigBee network, near field communication (NFC), intra-device bus, equipment Standby inner line, cable connection, or any combination thereof. In some embodiments, the network 150 may be a virtual private network. For example, the network 150 may be a network provided by a medical device manufacturer. In some embodiments, the network 150 may include one or more network access points. For example, the network 150 may include wired or wireless network access points such as base stations and/or internet exchange points through which one or more components of the device software processing system 100 may be connected to the network 150 to exchange data and/or information.

The software source 160 may provide various software components and/or relevant information. In some embodiments, the software source 160 may include the software components and/or information related to the software components (e.g., development information, release time, software type, applicable device type or model, software collection, user rating, user downloads, user clicks, updated information, and updated files). In some embodiments, the software source 160 may be provided by the manufacturer of the medical device. In some embodiments, the manufacturer may store the information related to the software components (e.g., development information, release time, software type, applicable device type or model, software collection, user rating, user downloads, user clicks, updated information, and updated files) to the software source 160. In some embodiments, the processing device 140 may obtain software components and/or update information thereof from the software source 160. In some embodiments, the software source 160 and the processing device 140 may be integrated.

In some embodiments, the software source 160 may be implemented on a storage device (e.g., a mass storage, a removable storage, a volatile read-and-write memory, a read-only memory (ROM), or the like, or any combination thereof). In some embodiments, the software source 160 may be implemented on a cloud platform.

It should be noted that the device software processing system 100 is provided for illustrative purposes only and is not intended to limit the scope of the present disclosure. For those skilled in the art, many changes and modifications can be made under the guidance of the content of the present disclosure. The features, structures, methods, and other features of the exemplary embodiments described herein may be combined in various ways to obtain additional and/or alternative exemplary embodiments. However, these changes and modifications may not deviate from the scope of the present disclosure. For example, the device software processing system 100 may also include a storage device used to store data and/or instructions.

Figure 2:
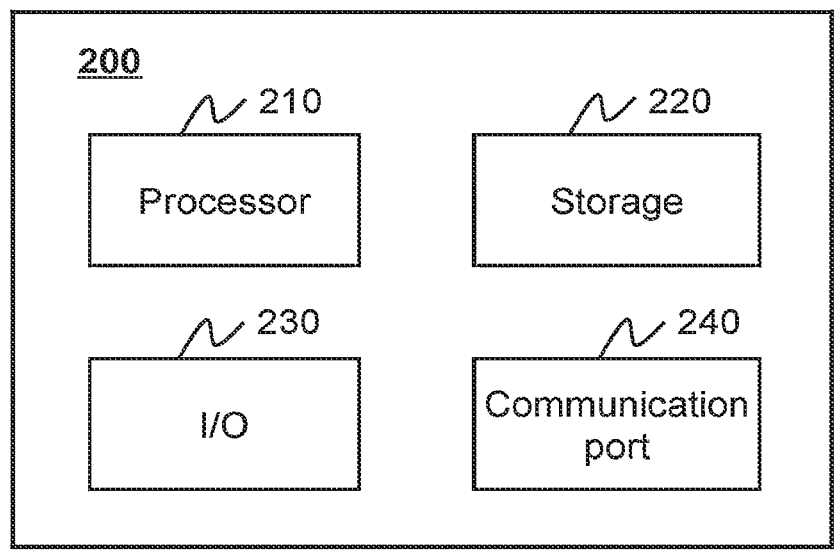
FIG. 2 is a schematic diagram illustrating exemplary hardware and/or software components of an exemplary computing device according to some embodiments of the present disclosure.

FIG. 2 is a schematic diagram illustrating exemplary hardware and/or software components of an exemplary computing device according to some embodiments of the present disclosure. In some embodiments, the processing device 140 and/or the operating terminal 120 may be implemented via the computing device 200. As illustrated in FIG. 2, the computing device 200 may include a processor 210, a storage 220, an input/output (I/O) 230, and a communication port 240.

The processor 210 may execute computer instructions (e.g., program code) and perform corresponding functions (e.g., functions of the processing device 140) in accordance with techniques described herein. The computer instructions may include, for example, routines, programs, objects, components, data structures, procedures, modules, and functions, which perform particular functions described herein. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

In some embodiments, the processor 210 may include interface circuits and processing circuits therein. The interface circuits may be configured to receive electronic signals from bus, wherein the electronic signals encode structured data and/or instructions for the processing circuits to process. The processing circuits may conduct logic calculations, and then determine a conclusion, a result, and/or an instruction encoded as electronic signals. Then the interface circuits may send out the electronic signals from the processing circuits via the bus.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from other components. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods or processes described in the present disclosure.

The I/O 230 may input and/or output signals, data, information, etc. In some embodiments, the I/O 230 may enable a user interaction. In some embodiments, the I/O 230 may include an input device and an output device. The input device may include alphanumeric and other keys that may be input via a keyboard, a touch screen (e.g., with haptics or tactile feedback), a speech input, an eye tracking input, a brain monitoring system, or any other comparable input mechanism. The input information received through the input device may be transmitted to other components via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 150) to facilitate data communications. The communication port 240 may establish connections between the computing device 200 with other components. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
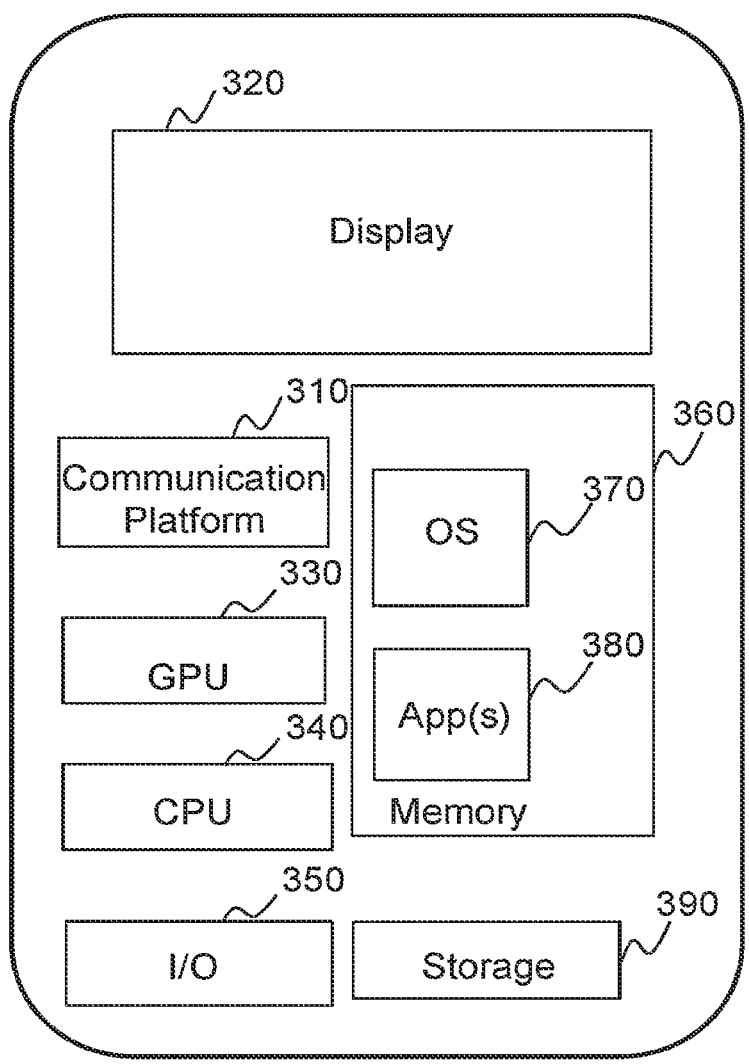
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to device software processing on the mobile device 300. User interactions with the information stream may be achieved via the I/O devices 350 and provided to other components of the device software processing system 100 via the networks 150.

Figure 4:
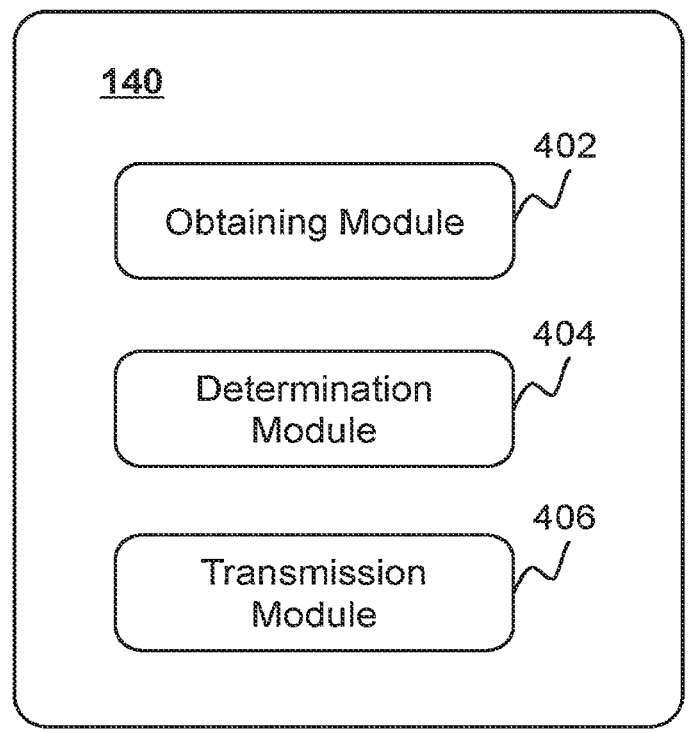
FIG. 4 is a block diagram illustrating an exemplary processing device according to some embodiments of the present disclosure.

FIG. 4 is a block diagram illustrating an exemplary processing device according to some embodiments of the present disclosure. As illustrated in FIG. 4, the processing device 140 may include an obtaining module 402, a determination module 404, and a transmission module 406.

The obtaining module 402 may be configured to receive, from an operating terminal of a target device, a target request with respect to a target software component. In some embodiments, the obtaining module 402 may be further configured to obtain account information of an account logged in through a user terminal and receive a candidate request with respect to at least one available software component from the user terminal. In some embodiments, the obtaining module 402 may be further configured to obtain device information of the medical device. In some embodiments, the obtaining module 402 may be further configured to obtain predictive usage information of the target device within a target time period.

The determination module 404 may be configured to determine a target file of the target software component based on the target request. In some embodiments, the determination module 404 may be configured to determine at least one medical device bound with the account, wherein the at least one medical device may include the target device. For one or more of the at least one medical device, the determination module 404 may be configured to determine at least one available software component. In some embodiments, the determination module 404 may be configured to determine a candidate software component based on the candidate request. In some embodiments, the determination module 404 may be configured to determine a recommended software component at least based on the device information and software information of the at least one available software component. In some embodiments, the determination module 404 may be further configured to determine a processing duration of the target software component based on the target file and determine a processing time schedule based on the predictive usage information and the processing duration.

The transmission module 406 may be configured to transmit the target file to the operating terminal of the target device to cause the operating terminal to perform a software processing operation on the target device based on the target file. In some embodiments, the transmission module 406 may be configured to transmit recommendation information of a recommended software component to the user terminal.

In some embodiments, the processing device 140 may include a recommendation module (which is not shown in the figures). The recommendation module may be configured to obtain account information of an account logged in through a user terminal, the account may be bound with the target device. The recommendation module may be configured to determine at least one medical device bound with the account, wherein the at least one medical device may include the target device. For one or more of the at least one medical device, the recommendation module may be configured to determine at least one available software component. The recommendation module may be configured to obtain device information of the medical device. The recommendation module may be configured to determine a recommended software component at least based on the device information and software information of the at least one available software component. The recommendation module may be configured to transmit recommendation information of the recommended software component to the user terminal.

More descriptions regarding the obtaining module 402, the determination module 404, and the transmission module 406 may be found in elsewhere in the present disclosure (e.g., FIG. 5 and the relevant descriptions thereof).

It should be noted that the above description of the processing device 140 and its modules is only for the convenience of description and does not limit this specification to the scope of the embodiments. It can be understood that for those skilled in the art, after understanding the principle of the system, they may combine the modules arbitrarily, or form a subsystem to connect with other modules without departing from this principle. In some embodiments, the obtaining module 402, the determination module 404, and the transmission module 406 may be different modules in a system or integrated into one module to realize functions of two or more modules. For example, the modules may share a same storage module, or each of the modules may include its respective storage module. Such deformations are within the scope of protection of the present disclosure.

FIG. 5 is a flowchart illustrating an exemplary process for device software processing according to some embodiments of the present disclosure. In some embodiments, process 500 may be executed by the device software processing system 100. For example, the process 500 may be implemented as a set of instructions (e.g., an application) stored in a storage device (e.g., the storage 220). In some embodiments, the processing device 140 (e.g., the processor 210 of the computing device 200 and/or one or more modules illustrated in FIG. 4) may execute the set of instructions and may accordingly be directed to perform the process 500. The operations of the illustrated process presented below are intended to be illustrative. In some embodiments, the process 500 may be accomplished with one or more additional operations not described and/or without one or more of the operations discussed. Additionally, the order of the operations of process 500 illustrated in FIG. 5 and described below is not intended to be limiting.

In 510, the processing device 140 (e.g., the obtaining module 402, the interface circuits of the processor 210) may receive, from an operating terminal (e.g., the operating terminal 120) of a target device (e.g., the target device 110), a target request (also referred to as a "target adding instruction") with respect to a target software component.

The target software component may refer to a software component that needs to be processed (e.g., to be installed, to be updated, to be uninstalled).

The target request may refer to a processing instruction with respect to the target software component. In some embodiments, the target request may include an installation instruction, an update instruction (also referred to as an "upgrade instruction"), an uninstall instruction, etc. Accordingly, the target software component may be referred to as a software component to be installed, a software component to be updated (also referred to as a "software component to be upgraded"), a software component to be uninstalled, etc. In some embodiments, the target request may also include a software identification of the target software component. In some embodiments, the software identification may include number, letter, symbol, or the like, or any combination thereof. In some embodiments, the target request may also include a processing type (e.g., installation, update, uninstallation).

In some embodiments, a user may determine a target software component among at least one candidate software component and trigger a corresponding target request. For example, the user may select a target software component among at least one candidate software component and click a corresponding button "update" to trigger the update instruction. In some embodiments, the at least one candidate software component may be determined through a user terminal (e.g., the user terminal 130). More descriptions regarding the candidate software component may be found in elsewhere in the present disclosure (e.g., FIG. 6 and the descriptions thereof).

In some embodiments, the user may determine the target software among at least one available software component and trigger a corresponding target request. For example, the user may select a target software component among at least one available software component (e.g., medical application) and click a corresponding button "update" to trigger the update instruction.

In some embodiments, the user may select all of the at least one candidate software component and/or the at least one available software component as the target software component(s) and trigger the corresponding target request (s). In some embodiments, the user may select part of the at least one candidate software component and/or the at least one available software component as the target software component(s) and trigger the corresponding target request (s).

In some embodiments, after the user triggers a plurality of target requests, the operating terminal may determine the plurality of target requests and transmit the plurality of target requests to the processing device 140 simultaneously. In some embodiments, after the user triggers the plurality of target requests, the operating terminal may determine the plurality of target requests and transmit the plurality of target requests to the processing device 140 in sequence. In some embodiments, after the user triggers the plurality of target requests, the operating terminal may determine the plurality of target requests and transmit the plurality of target requests to the processing device 140 in batches.

In some embodiments, the operating terminal and the processing device may communicate via the network 150. In some embodiments, in a medical scenario, it may be impossible for the operating terminal to communicate with the processing device 140 through a general network. In this situation, the communication between the operation terminal and the processing device 140 may be realized through a virtual private network (e.g., a switch). For example, the operating terminal may transmit the target request to the switch, and the switch may forward the target request to the processing device 140. The communication way between the operating terminal and the processing device 140 may not be limited in the present disclosure.

In 520, the processing device 140 (e.g., the determination module 404, the processing circuits of the processor 210) may determine a target file of the target software component based on the target request.

The target file may refer to a processing file (e.g., an install file, an update file, a uninstall file) that is required for processing (e.g., installing, updating, uninstalling) the target software component.

In some embodiments, the processing device 140 may determine a software identification and/or a processing type based on the target request and obtain the target file corresponding to the software identification and/or the processing type. For example, the processing device 140 may determine, based on the target request, the software identification of the target software component as "TX001" and the processing type as "installation," accordingly, the processing device 140 may obtain (e.g., download), from a storage device (e.g., the storage device 220, the software source 160), an installation file corresponding to TX001 as the target file corresponding to the target software component. As another example, the processing device 140 may determine, based on the target request, the software identification of the target software component as "TX002" and the processing type as "update," accordingly, the processing device 140 may obtain (e.g., download), from the storage device (e.g., the storage device 220, the software source 160), an update file corresponding to TX002 as the target file corresponding to the target software component.

In 530, the processing device 140 (e.g., the transmission module 406, the interface circuits of the processor 210) may transmit the target file to the operating terminal of the target device to cause the operating terminal to perform a software processing operation on the target device based on the target file.

In some embodiments, the processing device 140 may transmit the target file to the operating terminal of the target device in various ways. For example, the processing device 140 may transmit the target file to the operating terminal of the target device via the network 150 (e.g., optical network, device manufacturer network).

In some embodiments, after receiving the target file, the operating terminal may perform the software processing operation (e.g., software installation, software update, software uninstallation) on the target device based on the target file.

According to some embodiments of the present disclosure, the user can perform the software processing operation on the target device through the operating terminal autonomously, which can improve the self-selection of the user for software components corresponding to the target device, ensure the efficiency of the medical device software upgrade, and improve the user experience.

In some embodiments, the processing device 140 may also determine a target processing path of the target software component and transmit the target processing path of the target software component to the operating terminal. The operating terminal may process the target software component based on the target processing path. In some embodiments, after receiving the target file transmitted by the processing device 140, the operating terminal may determine the target processing path of the target software component.

The target processing path may refer to a processing path (e.g., a storage path) when the target software component is processed. In some embodiments, the target processing path may include an installation path, an update path, an uninstall path, etc.

In some embodiments, the processing device 140 or the operating terminal may obtain a historical processing path of the target software component and designate the historical processing path as the target processing path.

In some embodiments, the processing device 140 or the operating terminal may determine a storage state of the historical processing path and determine the target processing path based on the storage state and the target file. For example, the processing device 140 may determine a remaining storage space of the historical processing path and a size of the target file, if the remaining storage space is larger than the size of the target file and a difference between the remaining storage space and the size of the target file is larger than or equal to a preset threshold, the historical processing path may be determined as the target processing path; if the remaining storage space is larger than the size of the target file and the difference between the remaining storage space and the size of the target file is less than the preset threshold or the storage space is less than the size of the target file, other processing paths may be replaced, such as a path designated by the user, a largest path of the remaining storage space, etc.

According to some embodiments of the present disclosure, when the software processing operation is performed, a target processing path of the target software component may be determined, which can reduce a processing failure probability caused by insufficient storage space of the processing path and ensure a normal processing of the software in the target device.

It should be noted that the above descriptions are provided for the purposes of illustration, and not intended to limit the scope of the present disclosure. For persons having ordinary skills in the art, various variations and modifications may be conducted under the guidance of the present disclosure. However, those variations and modifications do not depart from the scope of the present disclosure.

FIG. 6 is a flowchart illustrating an exemplary process for determining a candidate software component according to some embodiments of the present disclosure. In some embodiments, process 600 may be executed by the device software processing system 100. For example, the process 600 may be implemented as a set of instructions (e.g., an application) stored in a storage device (e.g., the storage 220). In some embodiments, the processing device 140 (e.g., the processor 210 of the computing device 200 and/or one or more modules illustrated in FIG. 4) may execute the set of instructions and may accordingly be directed to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting.

In 610, the processing device 140 (e.g., the obtaining module 402, the interface circuits of the processor 210) may obtain account information of an account logged in through a user terminal (e.g., the user terminal 130).

In some embodiments, as described in connection with FIG. 1, the processing device 140 may be used as a software component management platform. Accordingly, a user may register an account and/or access the software component management platform through the operating terminal and/or the user terminal.

In some embodiments, the user may complete account registration through a user interface of the software component management platform. In some embodiments, the user may input registration information through the user interface and transmit the registration information to the processing device 140. The processing device 140 may receive the registration information of the user to complete the account registration. In some embodiments, the registration information may include name, gender, ID number, login account, login password, address, nature of work, work address, or the like, or any combination thereof. In some embodiments, the login account and/or the login password may be represented by characters, such as numbers, letters, symbols, or the like, or any combination thereof. For example, the login account may be mobile phone number, ID number, WeChat number, QQ number, or the like, or any combination thereof. As another example, the login password may be fingerprint password, digital password, letter password, image password, or the like, or any combination thereof. In some embodiments, the user may trigger a registration instruction through voice input, touch input, text input, etc.

In some embodiments, after completing the account registration, the account may be bound with a medical device (or referred to as be related with or referred to as determining a "mapping relationship" between the two). Under this condition, the account registration may include a device identification of the medical device (e.g., serial number, string). In some embodiments, the account registration may be completed first, then the account may be bound with the medical device when logging in. For example, after completing the account registration, the user may log in the software component management platform through the account and input the device identification of the medical device to complete the binding of the medical device and the account.

Figure 7:
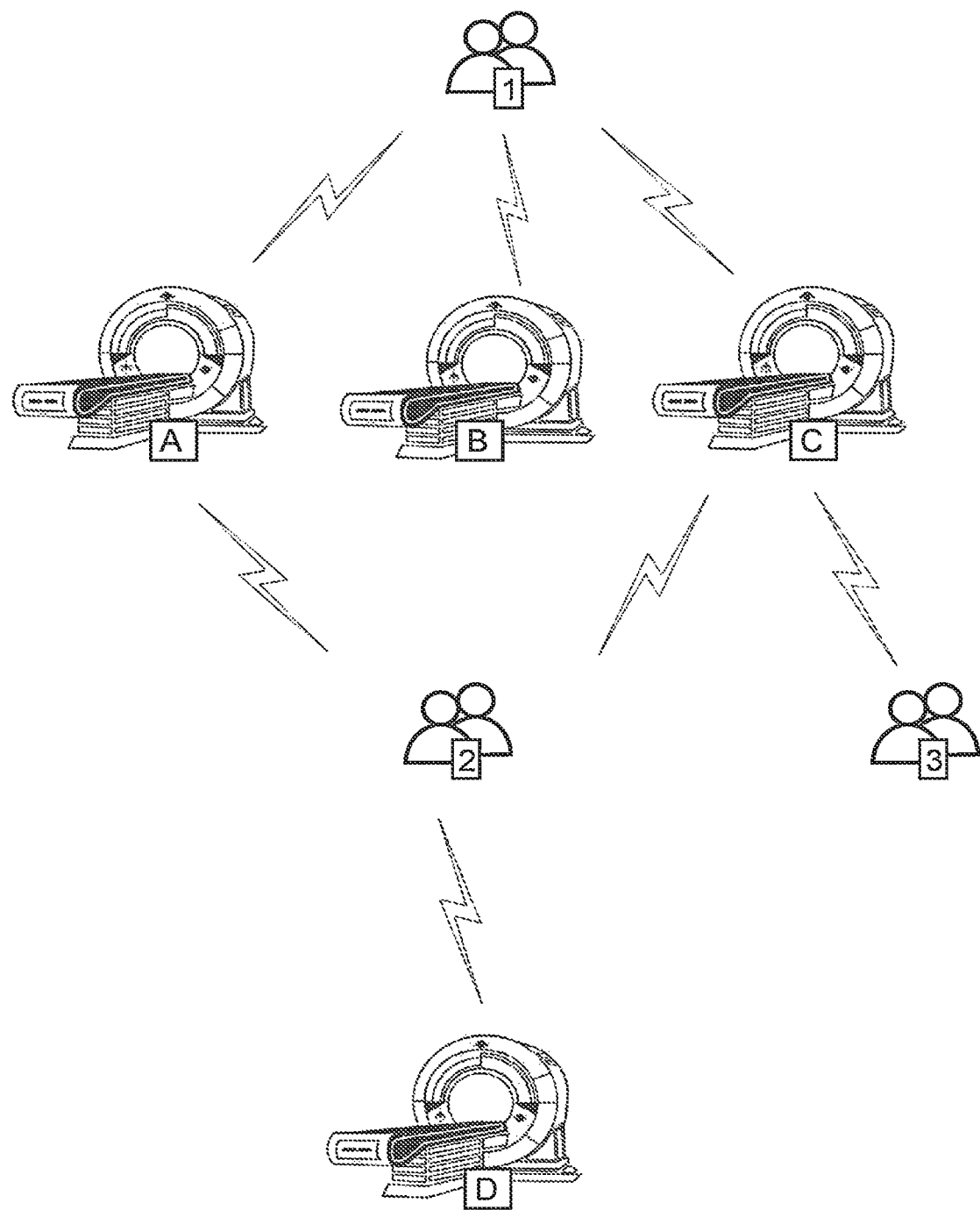
FIG. 7 is a schematic diagram illustrating bounding relationship among accounts and medical devices according to some embodiments of the present disclosure.

In some embodiments, one account may be bound with one or more medical devices. In some embodiments, one medical device may be bound with one or more accounts. For example, as shown in FIG. 7, account 1 may be bound with medical device A, medical device B, and medical device C; account 2 may be bound with medical device A, medical device C, and medical device D; account 3 may be bound with medical device C.

Figure 9A:
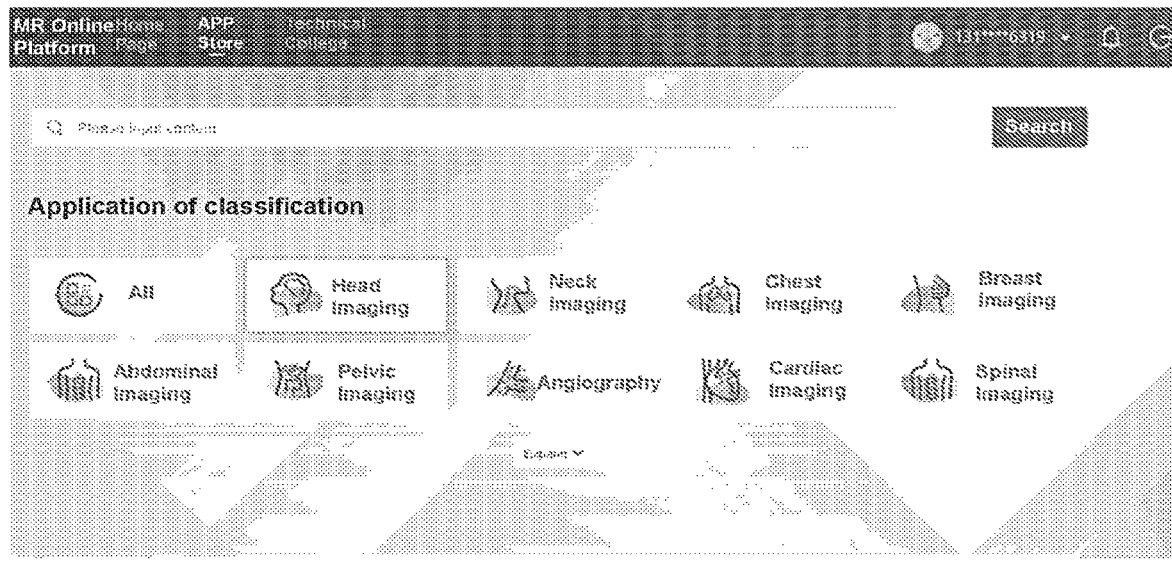
FIGS. 9A-9C are schematic diagrams illustrating a software component management platform displayed in an user terminal according to some embodiment of the present disclosure.
Figure 9B:

In some embodiments, after the user logs in the account through the user terminal, the processing device 140 may direct the user terminal to display the user interface of the software component management platform, wherein the account (or account information thereof) may be displayed in a preset position or a preset region (e.g., at an upper right corner) of the user interface. Merely for example, as shown in FIG. 9A, the user interface may display various software components (e.g., medical applications) associated with the medical device bound with the account by category (e.g., body parts), wherein a category identification may include icon (e.g., a head image) and/or name (e.g., "head imaging"). The user may click (e.g., through a mouse or a keyboard) the category identification to check software components (also can be referred to as "sub-software components") under this category. In some embodiments, taking a specific category as an example, the software components under this category may be sorted by a default order or by a preset rule (e.g., popularity, release time, usage frequency, common type). For example, as shown in FIG. 9B, after the user clicks a specific category identification, the processing device 140 may direct the user terminal to display software components under this category according to popularity. For convenience and brevity, FIG. 9A takes the account bound with merely one medical device as an example, it should be understood that if the account is bound with multiple medical devices, the processing device 140 may direct the user terminal to display software components associated with the multiple medical devices in columns or partitions.

Figure 9C:
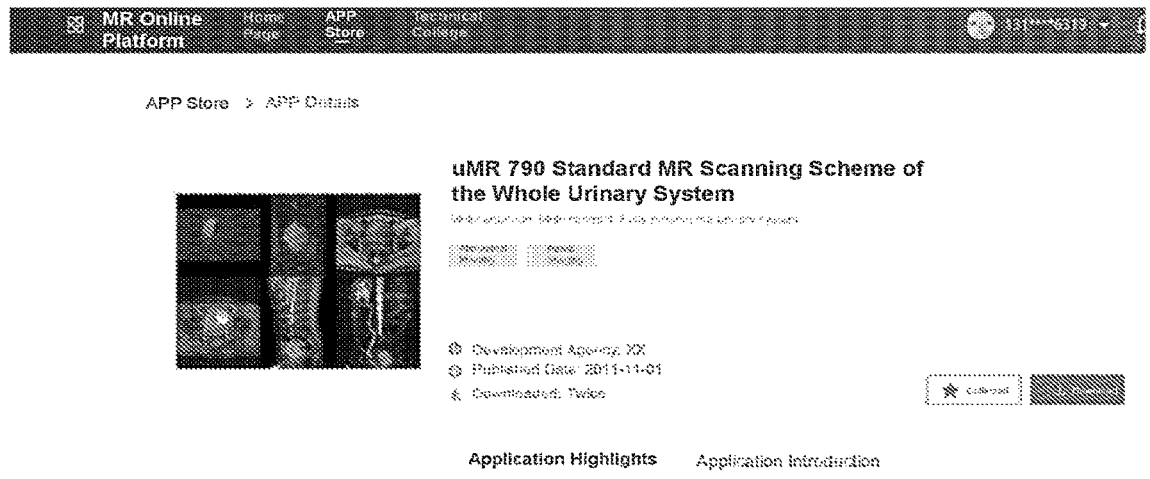

In some embodiments, the user may click an identification of any software component, then the user interface may display detail information of the software component, such as historical download record, software release time, development organization, application introduction, application highlight, whether it has been collected, application details, download control, or the like, or any combination thereof. For example, as shown in FIG. 9C, if the user clicks "UMR 790 Total Urinary System MR Standard Scanning Program Software," the user interface may display relevant information of this software component.

In some embodiments, the user interface may also display icon or text controls for other functions, such as close, remind, home page switch, menu expansion, software search window, search, or the like, or any combination thereof.

In some embodiments, when the user logs in the account through the user terminal, the processing device 140 may obtain the account information of the account. In some embodiments, the account information may include an account identification (e.g., serial number, string) of the account, device identification(s) (e.g., serial number, string) of at least one medical device bound with the account, or the like, or any combination thereof. In some embodiments, as described in connection with FIG. 5, the account may be bound with the target device. That is, the target device may be one of the at least one medical device bound with the account.

In some embodiments, the account information may also include an account permission of the account. In some embodiments, the account permission may reflect information that can be obtained after the account is logged in, operations that can be performed on the medical device, etc. For example, when the account permission of the account is lower than a preset threshold, only parts of target software components can be processed for the account. In some embodiments, if an account is bound with multiple medical devices, account permissions of the account may be different with respect to the multiple medical devices. For example, if a specific account is bound with a medical device A and a medical device B, an account permission of the account corresponding to the medical device A may be level 1; whereas an account permission corresponding to the medical device B may be level 2. In some embodiments, the account permission may be determined in various ways. For example, taking a medical device as an example, the medical device may correspond to at least one account with a highest level of account permission, wherein this account can modify account permissions of other accounts bound with this medical device.

In some embodiments, the account information may also include a user level. The user level may reflect information that can be obtained or displayed after the account is logged in, etc. For example, taking a hospital group including multiple branches as an example, an account (i.e., an account with a high user level) corresponding to the hospital group can be bound with all medical devices of the branches; whereas an account (i.e., an account with a low user level) corresponding to a branch only can be bound with medical device(s) of this branch.

In 620, the processing device 140 (e.g., the determination device 404, the processing circuits of the processor 210) may determine at least one medical device bound with the account.

In some embodiments, the processing device 140 may determine the at least one medical device bound with the account based on the account information. For example, the processing device 140 may determine the at least one medical device bound with the account based on device identification(s) in the account information. In some embodiments, the account may be an account bound with the target device, accordingly, the at least one medical device may include the target device.

In 630, for one or more of the at least one medical device, the processing device 140 (e.g., the determination module 404, the processing circuits of the processor 210) may determine at least one available software component.

In some embodiments, for one or more of the at least one medical device (one medical device will be taken as an example for convenience below), the processing device 140 may determine at least one available software component corresponding to the medical device. The available software component may refer to a software component available for the medical device.

In some embodiments, the at least one available software component may include applications with different functions. For example, the at least one available software component may include a magnetic resonance software component, a sequence application program, a protocol, a reconstruction program, a post-processing program, or the like, or any combination thereof. The magnetic resonance software component may refer to a software component necessary for running an MRI system, such as a magnetic resonance examination interactive software component, a magnetic resonance scanning control software component, a magnetic resonance service software component, etc. The sequence application program may refer to an organic combination of RF pulse and gradient pulse according to a preset timing in the process of magnetic resonance imaging. The protocol may refer to a set of parameters of the magnetic resonance device when performing a magnetic resonance scanning, such as scanning space position parameters, sequence parameters, coil parameters, reconstruction parameters, etc. The reconstruction program may include a program that converts the original data collected by the magnetic resonance system into image information through preset algorithms and/or processes. The post-processing program may refer to a program that performs a data processing and/or a data analysis (e.g., connection, segmentation, 3D reconstruction, contrast conditions, statistical analysis) on image data generated by the scanning of the magnetic resonance device.

In some embodiments, One or more of the at least one available software component may be decoupled. In some embodiments, the processing device 140 may layer various software components, compile the software components into different dynamic link libraries or executable programs, and design the different dynamic link libraries as one-way dependencies. Accordingly, when the upper software component(s) is processed, a normal operation of the underlying software component(s) would not be affected. In some embodiments, the processing device 140 may integrate software components easy to change and relevant configurations to achieve software component decoupling. For example, the processing device 140 may integrate a certain sequence software component and its dependent software component(s), configuration file(s), etc., to make that each sequence software component has its dependent module(s) and configuration(s) associated with its own operation. When a certain sequence software component needs to be processed, only the sequence software and its dependent software module(s) and configuration(s) need to be processed, other sequences software components and their dependent software modules and configurations do not need to be processed.

Merely for example, if a sequence software component A depends on a software component module X, a sequence software component B also depends on the software component module X. In general, the sequence software component A, the sequence software component B, and the software component module X may be designed as three mutually dependent software components. Under this condition, if the software component module X is processed due to business needs of the sequence software component A, since the sequence software component B depends on the software component module X, the sequence software component B would be forced to be processed, resulting in coupling between the sequence software component A and the sequence software component B. According to some embodiments of the present disclosure, the sequence software component A and the software component module X may be integrated into a sequence software component A+X and the sequence software component B and the software component module X may be integrated into a sequence software component B+X, so that the sequence software component A and sequence software component B may be processed independently without affecting each other. By decoupling the software components, when some of the software components are processed, the normal operation of other software components would not be affected, and the workload of the software processing operation can be reduced. Accordingly, the software processing process can be completed within a relatively short time, which can improve the software processing efficiency and the device use efficiency.

In some embodiments, the processing device 140 may determine a device type of the medical device based on the device identification of the medical device and determine the at least one available software component corresponding to the medical device based on the device type.

In some embodiments, the processing device 140 may direct the user terminal to display the at least one available software component through the user interface of the software component management platform. As described in connection with above, for example, as shown in FIG. 9A-FIG. 9C, the user interface may display icon, name, detail information, etc. of the at least one available software component.

Figure 9D:
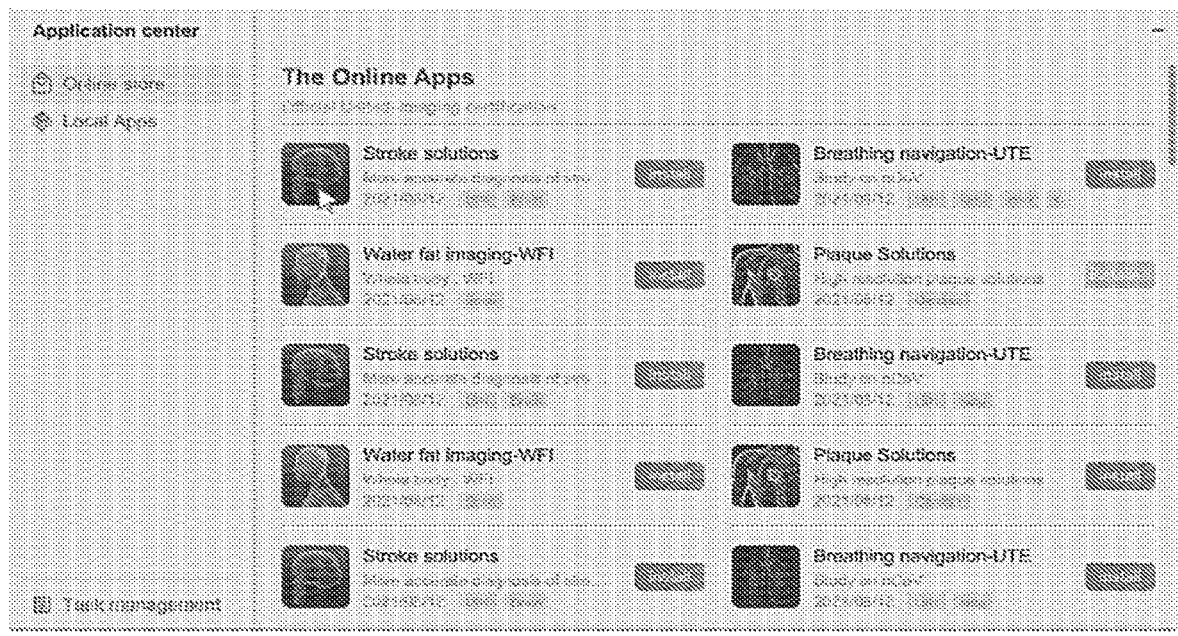
FIG. 9D is a schematic diagrams illustrating a software component management platform displayed in an operating terminal according to some embodiment of the present disclosure.

In some embodiments, the processing device 140 may further display at least one available software management platform through the operating terminal of the software component management platform. As shown in FIG. 9D, when the user logs in the software component management platform through the operating terminal, the interface of the operating terminal may display names (e.g., "Stroke solutions"), icons, user created area, user priority area, upgrade request time (e.g., "2021/08/12"), etc. of all available software components corresponding to the medical device corresponding to the operating terminal. As shown in FIG. 9D, "Stroke solutions" may represent the name of the software component, the corresponding "202/08/12" may represent the upgrade request time, "More accurate diagnosis of stro . . . " may represent a brief introduction of the software component, and the left rounded image may represent the icon of the software component.

In some embodiments, the at least one available software component may be displayed in various visual forms (e.g., text form, view form), which is not limited in the present disclosure.

In some embodiments, the user interface may merely display the at least one available software component. In some embodiments, the user interface may display the at least one available software component and other software component(s), and the at least one available software component may be displayed differently from other software component(s). For example, a font color of the at least one available software component may be different from font color(s) of other software component(s).

In 640, the processing device 140 (e.g., the obtaining module 402, the interface circuits of the processor 210) may receive a candidate request with respect to the at least one available software component from the user terminal.

In some embodiments, the user may browse the at least one available software component and/or view the detail information of the at least one available software, and further determine an interested candidate software component. Accordingly, the candidate request may be an instruction (e.g., a collect instruction) with respect the interested candidate software. Merely for example, as shown in FIG. 9C, the user may click a "collection" button corresponding to the "uMR 790" software component to trigger the candidate request with respect to the software component.

In some embodiments, the user may download the documentation of at least one available component to the user terminal. As shown in FIG. 9C, the user may download the installation document of the available component to the user terminal that is using currently by clicking "download".

In some embodiments, the candidate request may include the account information, the software identification of the interested candidate software component, or the like, or any combination thereof. In some embodiments, the candidate request may also include a device identification corresponding to the medical device.

In 650, the processing device 140 (e.g., the determination module 404, the processing circuits of the processor 210) may determine a candidate software component based on the candidate request.

In some embodiments, after receiving the candidate request transmitted by the user terminal, the processing device 140 may determine the corresponding candidate software component. In some embodiments, the processing device 140 may determine the account information that transmits the candidate request. In some embodiments, the candidate software component may determine through the user terminal and/or the account information may be synchronized to a corresponding operating terminal of the medical device. Accordingly, the user can select the target software component from the candidate software component (s) through the operating terminal.

According to some embodiments of the present disclosure, the user can browse information associated with at least one available software component at anytime and anywhere through the user terminal, and add the interested software component as the candidate software component, which can improve the autonomous selectivity of the user.

In some embodiments, when the medical device is bound with a plurality of accounts, the candidate software components determined by the plurality of accounts may be shared among the plurality of accounts. For example, as shown in FIG. 7A, account(s) bound with medical device C may include account 1, account 2, and account 3, and candidate software components corresponding to medical device C added by account 1, account 2, and account 3 may be shared among account 1, account 2, and account 3. In some embodiments, the candidate software components shared among the plurality of accounts may be associated with the account permission corresponding to each of the plurality of accounts. For example, if the user and the other users are bound with a same medical device and account permissions of the other users are not higher than an account permission of the user, a user can browse candidate software components corresponding to the medical device determined by the other users. In some embodiments, sharing information among the plurality of accounts may also include account identifications corresponding to the plurality of accounts. Accordingly, a user (or an account) who adds a specific candidate software component can be determined based on the account identification. In some embodiments, the candidate software components may determine through the user terminal and/or the account information may be synchronized to a corresponding operating terminal of the medical device. Accordingly, the user can select the target software component from the candidate software component(s) through the operating terminal.

According to some embodiments of the present disclosure, candidate software components determined by a plurality of accounts bound with a same medical device may be shared among the plurality of accounts, which can avoid repeated adding instructions executed by the plurality of accounts (or users), thereby improving operation efficiency and saving software processing time.

Figure 8:
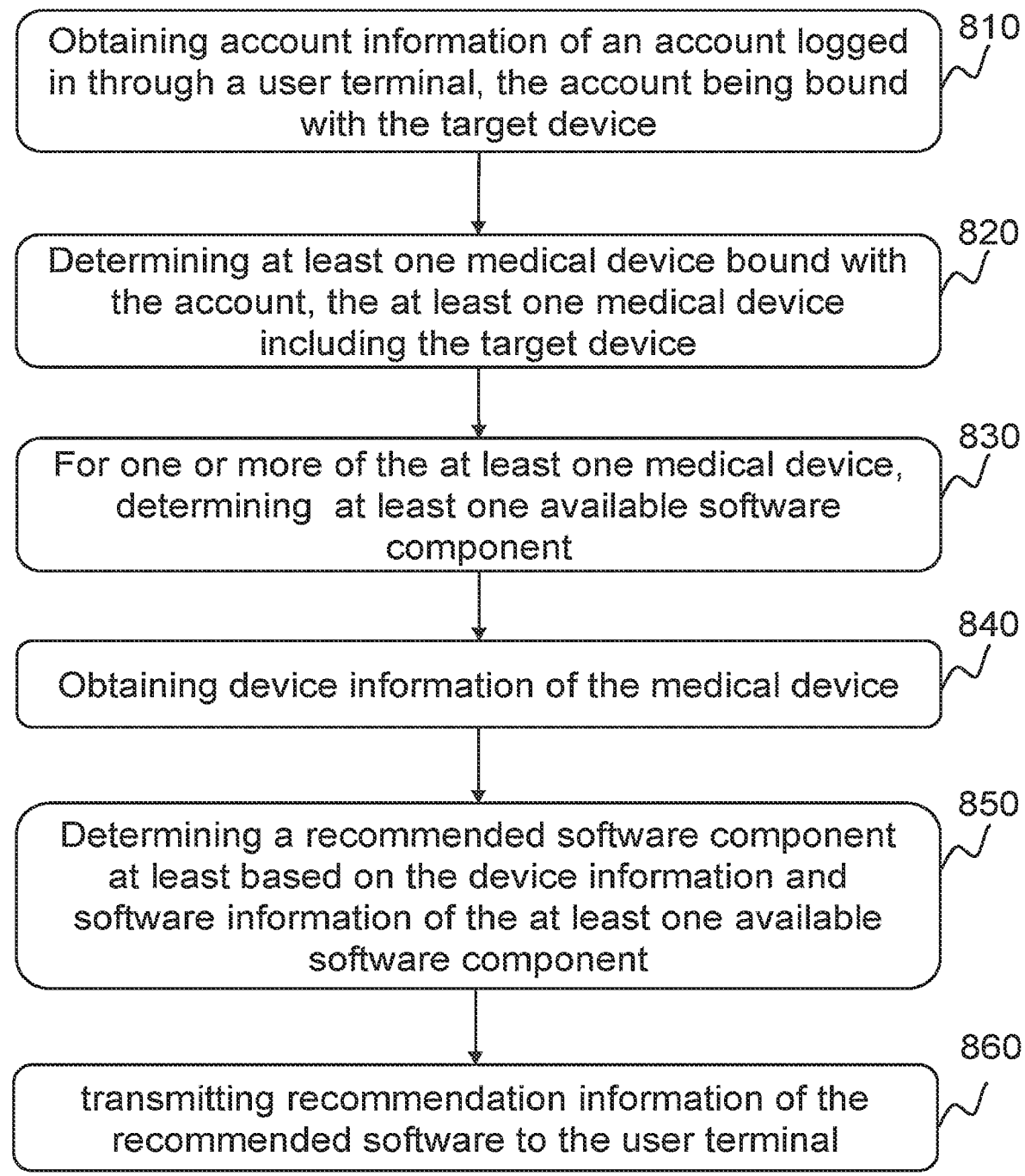
FIG. 8 is a flowchart illustrating an exemplary process for determining at least one recommended software component according to some embodiments of the present disclosure.

FIG. 8 is a flowchart illustrating an exemplary process for determining at least one recommended software component according to some embodiments of the present disclosure. In some embodiments, process 800 may be executed by the device software processing system 100. For example, the process 800 may be implemented as a set of instructions (e.g., an application) stored in a storage device (e.g., the storage 220). In some embodiments, the processing device 140 (e.g., the processor 210 of the computing device 200 and/or one or more modules illustrated in FIG. 4) may execute the set of instructions and may accordingly be directed to perform the process 800. The operations of the illustrated process presented below are intended to be illustrative. In some embodiments, the process 800 may be accomplished with one or more additional operations not described and/or without one or more of the operations discussed. Additionally, the order of the operations of process 800 illustrated in FIG. 8 and described below is not intended to be limiting.

In 810, the processing device 140 (e.g., the obtaining module 402, the interface circuits of the processor 210) may obtain account information of an account logged in through a user terminal (e.g., the user terminal 130). More relevant descriptions may be found in operation 610.

In 820, the processing device 140 (e.g., the determination module 404, the processing circuits of the processor 210) may determine at least one medical device bound with the account. In some embodiments, the at least one medical device including the target device. More relevant descriptions may be found in operation 620.

In 630, for one or more of the at least one medical device, the processing device 140 (e.g., the determination module 404, the processing circuits of the processor 210) may determine at least one available software component. More relevant descriptions may be found in operation 630.

In 840, the processing device 140 (e.g., the obtaining module 402, the processing circuits of the processor 210) may obtain device information of the medical device.

As used herein, device information may refer to information associated with the medical device. In some embodiments, the device information may include but is not limited to a device model, a device identification, a device configuration, a device usage duration, a historical scanning type, historical software information of the medical device, or the like, or any combination thereof.

In some embodiments, the processing 140 may obtain the device information through various ways. For example, the processing device 140 may determine the device identification and/or the device type of the medical device according to an input of the user. As another example, the operating terminal may store usage data (e.g., the device usage duration, the historical scanning type) of the medical device and may upload the usage data to the processing device 140 in response to a permission or an instruction.

In 850, the processing device 140 (e.g., the determination module 404, the processing circuits of the processor 210) may determine a recommended software component at least based on the device information and software information of the at least one available software component.

In some embodiments, the processing device 140 may analyze and process the device information and the software information of the at least one available software component by modeling or using various data analysis algorithms (e.g., regression analysis, discriminant analysis) to determine the recommended software component. For example, the processing device 140 may determine a most frequent scanning type of the medical device based on the device information of the medical device, determine available software components corresponding to the scanning type based on the software information of the at least one available software component, and determine the recommended software component that satisfies a preset condition (e.g., downloads are greater than a preset download threshold) as the recommended software component.

In some embodiments, the processing device 140 may determine a recommendation score of each of the at least one available software component at least based on the device information and the software information of the at least one available software component according to a recommendation model. In some embodiments, an input of the recommendation model may be the device information and the software information of the at least one available software component, and an output of the recommendation model may be a recommendation score of each of the at least one available software component. In some embodiments, the recommendation score may be represented in various ways. For example, the recommendation score may be represented as a number within 0-10, the higher the recommendation score is, the more the available software component may be recommended to the user. More descriptions of the recommendation model may be found in FIG. 10 and descriptions thereof.

Further, the processing device 140 may determine the recommended software component from the at least one available software component based on the recommendation score of each of the at least one available software component. For example, the processing device 140 may determine an available software component with a recommendation score greater than a preset score threshold as the recommended software component.

In some embodiments, the processing device 140 may also obtain network environment information and/or scanning requirement information of the target device. In some embodiments, the network environment information may include network status, network rate, bandwidth, or the like, or any combination thereof. In some embodiments, the network environment information or the scanning requirement information may be determined in various ways. For example, the processing device 140 may obtain the network environment information by detecting an network environment of the medical device. As another example, the processing device 140 may determine the scanning requirement information based on the historical scanning information of the medical device.

In some embodiments, the processing device may determine at least one candidate recommended software component from the at least one available software component based on the recommendation score of each of the at least one available software component. For example, the processing device 140 may determine the available software component that the recommendation score is greater than a second preset threshold as the candidate recommended software component. Further, the processing device 140 may determine the recommended software component from the at least one candidate recommended software component by processing at least one of the network environment information, the scanning requirement information, or the software information of the at least one candidate recommended software component.

In some embodiments, the processing device 140 may determine the recommended software component from the at least one candidate recommended software component by processing at least one of the network environment information, the scanning requirement information, or the software information of the at least one candidate recommended software component by modeling or using various data analysis algorithms (e.g., regression analysis, discriminant analysis).

In some embodiments, the processing device 140 may determine the recommended software component by processing at least one of the network environment information, the scanning requirement information, or the software information of the at least one candidate recommended software component by a software determination model. In some embodiments, an input of the software determination model may include the network environment information, the scanning requirement information, and/or the software information of the at least one candidate recommended software component, and an output of the software determination model may include the recommended software component. In some embodiments, the processing device 140 may determine the software determination model based on training samples, wherein a training sample may include historical network environment information, historical scanning requirement information, and sample software information of at least one sample candidate recommended software component, and a training label of the training sample may be a sample recommended software component. In some embodiments, the historical network environment information and the historical scanning requirement information in the training samples may be obtained from historical data of medical devices, and the sample candidate recommended software components and corresponding training labels may be obtained based on user marks. The processing device 140 may input the training samples into an initial determination model and iteratively update parameters of the initial determination model based on a preset loss function until a preset training condition is satisfied. The preset training condition may include but not limited to loss function convergence, training period reaching threshold, etc.

In some embodiments, the determination model may be integrated into the recommendation model to be as a layer of the recommendation model.

In 860, the processing device 140 (e.g., the transmission module 406, the interface circuits of the processor 210) may transmit recommendation information of the recommended software component to the user terminal.

In some embodiments, the recommendation information may include name, function, rating, historical download amount, etc., of the recommended software component, or any combination thereof.

In some embodiments, the processing device 140 may transmit the recommendation information of the recommended software component to the user terminal in various ways. For example, the processing device 140 may transmit the recommendation information to a publish column of the user terminal.

According to some embodiments of the present disclosure, by analyzing software information of available software component(s) and the device information, an appropriate software component can be recommended more accurately and the user experience and the software processing efficiency can be improved.

Figure 10:
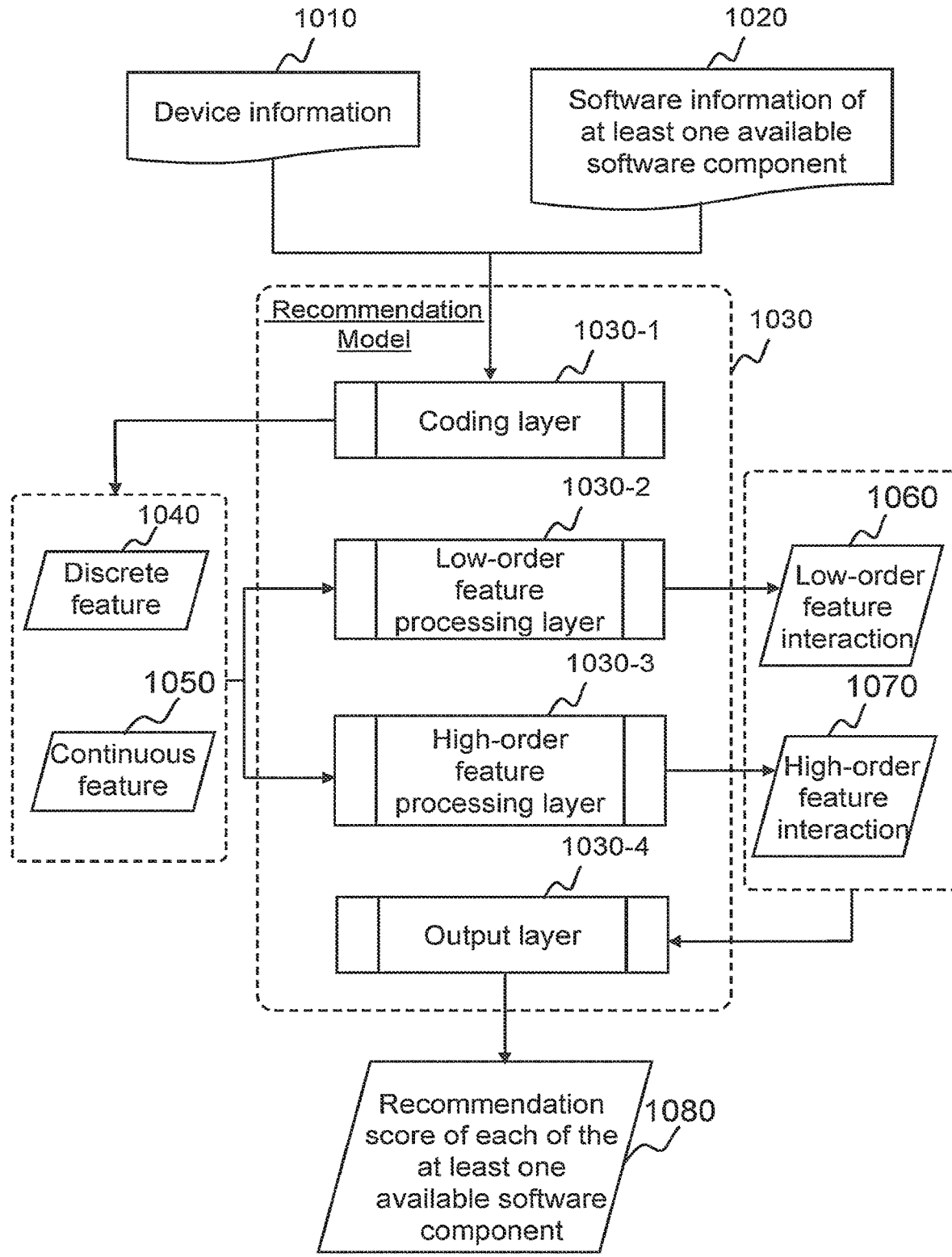
FIG. 10 is a schematic diagram illustrating an exemplary process for determining a recommendation score of an available software component according to some embodiments of the present disclosure.

FIG. 10 is a schematic diagram illustrating an exemplary process for determining a recommendation score of an available software component according to some embodiments of the present disclosure.

As shown in FIG. 10, the processing device 140 may input device information 1010 and software information 1020 of at least one available software component into a recommendation model 1030 to determine a recommendation score 1080 of each of the at least one available software component.

In some embodiments, the recommendation model 1030 may include a coding layer 1030-1, a low-order feature processing layer 1030-2, a high-order feature processing layer 1030-3, and an output layer 1030-4.

The coding layer 1030-1 may extract numerical features (e.g., device usage duration, user clicks, user downloads, user favorites) in the device information and the software information of the at least one available software component to obtain a corresponding discrete feature 1040. The coding layer 1030-1 may extract type features (e.g., device type, software type, device configuration) in the device information and the software information of the at least one available software component to obtain a correspondingly continuous feature 1050. In some embodiments, the coding layer 1030-1 may include but not limited to BERT (Bidirectional Encoder Representations from Transformers), one-hot, etc.

In some embodiments, the recommendation module 1030 may further include an embedded layer (not shown) user to obtain low-dimensional dense discrete features by reducing dimension of high-dimensional sparse discrete features.

In some embodiments, the recommendation model 1030 may further include a splicing layer (not shown) used to splice the discrete feature and the continuous feature, and input the spliced feature into the low-order feature processing layer 1030-2 and the high-order feature processing layer 1030-3.

The low-order feature processing layer 1030-2 may determine a low-order feature interaction result 1060 by processing (e.g., performing a second-order feature interaction) the discrete feature 1040 and the continuous feature 1050. In some embodiments, the low-order feature processing layer 1030-2 may be FM (Factorization Machine).

The high-order feature processing layer 1030-3 may determine a high-order feature interaction result 1070 by processing (e.g., performing a high-order feature interaction) the discrete feature 1040 and the continuous feature 1050. In some embodiments, the high-order feature processing layer 1030-3 may be DNN (Deep Neural Networks).

The output layer 1030 may determine a recommendation score 1080 of each of the at least one available software component by processing the low-order feature interaction result 1060 and the high-order feature interaction result 1070. In some embodiments, the output layer 1030-4 may be a full connection layer.

In some embodiments, the processing device 140 may obtain the recommendation model 1030 by training an initial recommendation model based on a plurality of training samples. The training sample may include sample device information of a sample device and sample software information of at least one sample available software component, and a sample label may include a sample recommendation score corresponding to each of the at least one sample available software component. In some embodiments, the sample device information in the training sample may be obtained based on historical data of the sample device, the sample software information of the at least one sample available software component may be obtained from a database, and the sample recommendation score corresponding to each of the at least one sample available software component may be determined based on historical software information of the sample device or based on user marks. For example, the processing device 140 may determine historical software components in the sample device based on the historical software information. For a certain sample available software component, when the historical software components include the sample available software component, the processing device 140 may determine the recommendation score of the sample available software component as 1; when the historical software components include the sample available software component, the processing device 140 may determine the recommendation score of the sample available software component as 0.

The processing device 140 may input the training samples into an initial determination model and iteratively update parameters of the initial determination model based on a preset loss function until a preset training condition is satisfied. The preset training condition may include but not limited to loss function convergence, training period reaching threshold, etc.

According to some embodiments of the present disclosure, by processing the device information and the software information of the at least one available software component through a machine learning model, the processing efficiency and the accuracy of the recommendation score can be improved. Further, the recommendation model may be set as a structure of Deep+FM, which can fully mine hidden information in data, ensure interaction between the discrete feature and the continuous feature, reduce the computational complexity, and further improve the accuracy of the output recommendation score.

FIG. 11 is a flowchart illustrating an exemplary process for determining a processing time schedule of a target software component according to some embodiments of the present disclosure. In some embodiments, process 1100 may be executed by the device software processing system 100. For example, the process 1100 may be implemented as a set of instructions (e.g., an application) stored in a storage device (e.g., the storage 220). In some embodiments, the processing device 140 (e.g., the processor 210 of the computing device 200 and/or one or more modules illustrated in FIG. 4) may execute the set of instructions and may accordingly be directed to perform the process 1100. The operations of the illustrated process presented below are intended to be illustrative. In some embodiments, the process 1100 may be accomplished with one or more additional operations not described and/or without one or more of the operations discussed. Additionally, the order of the operations of process 1100 illustrated in FIG. 11 and described below is not intended to be limiting.

In 1110, the processing device 140 (e.g., the obtaining module 402, the interface circuits of the processor 210) may obtain predictive usage information of the target device within a target time period.

The target time period may refer to an expected time period or a planning time period during which a target software component is intended to be processed.

The predictive usage information may refer to a predictive usage condition of the target device within the target time period. In some embodiments, the predictive usage information may include an idle condition of the target device within the target time period, sub-time periods within the target time period, an idle condition of the target device within each sub-time period, or the like, or any combination thereof.

In some embodiments, the processing device 140 may obtain the predictive usage information of the target device within the target time period in various ways. For example, the processing device 140 may obtain the predictive usage information of the target device in a historical time period (e.g., a historical time period similar to the target time period), and determine the predictive usage information of the target device within the target time period by processing the device usage information by modeling or using various data analysis algorithms (e.g., regression analysis, discriminant analysis).

In 1120, the processing device 140 (e.g., the determination module 404, the processing circuits of the processor 210) may determine a processing duration of the target software component based on the target file.

The processing duration may refer to a duration required for the processing of the target software component, for example, a duration required for installing the target software component, a duration required for updating the target software component, a duration required for uninstalling the target software component, etc.

In some embodiments, the processing device 140 may determine the processing duration by analyzing the target file. For example, the processing device 140 may obtain historical processing data of the target device and determine a corresponding relationship between file size and processing time. Then the processing device 140 may determine the processing duration of the target software according to a size of the target file and the relationship.

In 1130, the processing device 140 (e.g., the determination module 404, the processing circuits of the processor 210) may determine a processing time schedule based on the predictive usage information and the processing duration.

The processing time schedule may refer to a schedule for the processing of the target software component within the target time period. For example, if there are multiple target software components, the processing time schedule may include a processing sequence of the multiple target software components within the target time period, a processing start time, a processing end time, or the like, or any combination thereof.

In some embodiments, the processing device 140 may determine an idle duration of the target device in the target time period, when a difference between the idle duration and the processing duration of the target software component is greater than a preset difference threshold, the processing device 140 may determine the idle duration as a duration for processing the target software component within the target time period.

In some embodiments, when multiple target software components need to be processed within the target time period, the processing device 140 may determine a processing sequence of the multiple target software components. For example, the processing device 140 may determine an idle duration of the target device within the target time period based on the predictive usage information. The processing device 140 may determine the target software components that can be processed within the idle duration based on the idle duration and the processing duration corresponding to each of the multiple target software components. Then the processing device 140 may determine a processing sequence of the target software components based on the recommendation scores of the target software components that can be processed in the idle duration.

According to some embodiments of the present disclosure, by processing the predictive usage information of the target device and the processing duration of the target software component, the processing duration schedule of the target software component may be determined, which can avoid affecting the normal use of the target device and maximize the software processing efficiency of the target device.

The present disclosure may also provide a system for device software processing. The system may include at least one storage device including a set of instructions and at least one processor configured to communicate with the at least one storage device. When executing the set of instructions, the at least one processor is configured to direct the system to perform operations including receiving, from an operating terminal of a target device, a target request with respect to a target software component; determining a target file of the target software component based on the target request; and transmitting the target file to the operating terminal of the target device to cause the operating terminal to perform a software processing operation on the target device based on the target file.

The present disclosure may also provide a non-transitory computer readable medium including executable instructions. When executed by at least one processor, the executable instructions may direct the at least one processor to perform a method, the method including: receiving, from an operating terminal of a target device, a target request with respect to a target software component; determining a target file of the target software component based on the target request; and transmitting the target file to the operating terminal of the target device to cause the operating terminal to perform a software processing operation on the target device based on the target file.

The basic concepts have been described. Obviously, for those skilled in the art, the detailed disclosure may be only an example and may not constitute a limitation to the present disclosure. Although not explicitly stated here, those skilled in the art may make various modifications, improvements, and amendments to the present disclosure. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of the specification are not necessarily all referring to the same embodiment. In addition, some features, structures, or features in the present disclosure of one or more embodiments may be appropriately combined.

Moreover, unless otherwise specified in the claims, the sequence of the processing elements and sequences of the present application, the use of digital letters, or other names are not used to define the order of the application flow and methods. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various assemblies described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure and aiding in the understanding of one or more of the various embodiments. However, this disclosure may not mean that the present disclosure object requires more features than the features mentioned in the claims. In fact, the features of the embodiments are less than all of the features of the individual embodiments disclosed above.

At last, it should be understood that the embodiments described in the disclosure are used only to illustrate the principles of the embodiments of this application. Other modifications may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A software upgrading method for a medical device, comprising:
   receiving, from an operating terminal of a target device, a target request with respect to a target software component;
   determining a target file of the target software component based on the target request; and
   transmitting the target file to the operating terminal of the target device to cause the operating terminal to perform a software processing operation on the target device based on the target file;
   wherein the target software component is among at least one candidate software component, and the method further includes:
   obtaining account information of an account logged in through a user terminal, the account being bound with the target device;

determining at least one medical device bound with the account, the at least one medical device including the target device;

for one or more of the at least one medical device, determining at least one available software component;

receiving a candidate request with respect to the at least one available software component from the user terminal; and determining a candidate software component based on the candidate request.

2. The method of claim 1, wherein one or more of the at least one available software components are decoupled.

3. The method of claim 1, wherein for one or more of the at least one medical device, when the medical device is bound with a plurality of accounts, candidate software components determined through the plurality of accounts are shared among the plurality of accounts.

4. The method of claim 3, wherein sharing information includes account identifiers corresponding to the plurality of accounts, respectively.

5. The method of claim 1, wherein the method further includes:

obtaining device information of the medical device;

determining a recommended software component at least based on the device information and software information of the at least one available software component; and transmitting recommendation information of the recommended software component to the user terminal.

6. The method of claim 5, wherein the determining the recommended software component at least based on the device information and the software information of the at least one available software component includes:

determining a recommendation score of each of the at least one available software component at least based on the device information and the software information of the at least one available software component according to a recommendation model; and determining the recommended software from the at least one available software component based on the recommendation score of each of the at least one available software component.

7. The method of claim 6, wherein the recommendation model includes a coding layer, a low-order feature processing layer, a high-order feature processing layer, and an output layer; and the determining the recommendation score of each of the at least one available software component at least based on the device information and the software information of the at least one available software component according to the recommendation model includes:

determining, through the coding layer, a discrete feature and a continuous feature by at least processing the device information and the software information of the at least one available software component;

determining, through the low-order feature processing layer, a low-order feature interaction result by processing the discrete feature and the continuous feature;

determining, through the high-order feature processing layer, a high-order feature interaction result by processing the discrete feature and the continuous feature; and determining, through the output layer, the recommendation score of each of the at least one available software component by processing the low-order feature interaction result and the high-order feature interaction result.

8. The method of claim 6, wherein the determining the recommended software from the at least one available software component based on the recommendation score of each of the at least one available software component includes:

obtaining at least one of network environment information or scanning requirement information of the medical device;

determining at least one candidate recommended software component from the at least one available software component based on the recommendation score of each of the at least one available software component; and determining the recommended software from the at least one candidate recommended software by processing at least one of the network environment information, the scanning requirement information, or the software information of the at least one candidate recommended software.

9. The method of claim 1, wherein the method further includes:

obtaining predictive usage information of the target device within a target time period;

determining a processing duration of the target software component based on the target file; and determining a processing time schedule based on the predictive usage information and the processing duration.

10. A software upgrading system for a medical device, comprising:

a storage device storing a set of instructions;

at least one processor in communication with the storage device, wherein when executing the set of instructions, the at least one processor is configured to direct the system to perform operations including:

receiving, from an operating terminal of a target device, a target request with respect to a target software component;

determining a target file of the target software component based on the target request; and transmitting the target file to the operating terminal of the target device to cause the operating terminal to perform a software processing operation on the target device based on the target file;

wherein the target software component is among at least one candidate software component, and the operations further include:

obtaining account information of an account logged in through a user terminal, the account being bound with the target device;

determining at least one medical device bound with the account, the at least one medical device including the target device;

for one or more of the at least one medical device, determining at least one available software component;

receiving a candidate request with respect to the at least one available software component from the user terminal; and determining a candidate software component based on the candidate request.

11. The system of claim 10, wherein for one or more of the at least one medical device, when the medical device is bound with a plurality of accounts, candidate software components determined through the plurality of accounts are shared among the plurality of accounts.

12. The system of claim 10, wherein the at least one processor is further directed to:

obtaining device information of the medical device;
determining a recommended software at least based on the device information and software information of the at least one available software component; and
transmitting recommendation information of the recommended software to the user terminal.

13. The system of claim 12, wherein the determining the recommended software component at least based on the device information and the software information of the at least one available software component includes:
determining a recommendation score of each of the at least one available software component at least based on the device information and the software information of the at least one available software component according to a recommendation model; and
determining the recommended software from the at least one available software component based on the recommendation score of each of the at least one available software component.

14. The system of claim 13, wherein
the recommendation model includes a coding layer, a low-order feature processing layer, a high-order feature processing layer, and an output layer; and
wherein the determining the recommendation score of each of the at least one available software component at least based on the device information and the software information of the at least one available software component according to the recommendation model includes:
determining, through the coding layer, a discrete feature and a continuous feature by at least processing the device information and the software information of the at least one available software component;
determining, through the low-order feature processing layer, a low-order feature interaction result by processing the discrete feature and the continuous feature;
determining, through the high-order feature processing layer, a high-order feature interaction result by processing the discrete feature and the continuous feature; and
determining, through the output layer, the recommendation score of each of the at least one available software component by processing the low-order feature interaction result and the high-order feature interaction result.

15. The system of claim 14, wherein the determining the recommended software from the at least one available software component based on the recommendation score of each of the at least one available software component includes:
obtaining at least one of network environment information or scanning requirement information of the target device;
determining at least one candidate recommended software component from the at least one available software component based on the recommendation score of each of the at least one available software component; and
determining the recommended software from the at least one candidate recommended software component by processing at least one of the network environment information, the scanning requirement information, or the software information of the at least one candidate recommended software component.

16. A non-transitory computer readable medium, comprising executable instructions that, when executed by at least one processor, direct the at least one processor to perform a method, the method comprising:
receiving, from an operating terminal of a target device, a target request with respect to a target software component;
determining a target file of the target software component based on the target request; and
transmitting the target file to the operating terminal of the target device to cause the operating terminal to perform a software processing operation on the target device based on the target file;
wherein the target software component is among at least one candidate software component, and the method further includes:
obtaining account information of an account logged in through a user terminal, the account being bound with the target device;
determining at least one medical device bound with the account, the at least one medical device including the target device;
for one or more of the at least one medical device,
determining at least one available software component;
receiving a candidate request with respect to the at least one available software component from the user terminal; and
determining a candidate software component based on the candidate request.

* * * * *